United States Patent [19]

Norden-Paul et al.

[11] Patent Number: 4,878,175

[45] Date of Patent: Oct. 31, 1989

[54] METHOD FOR GENERATING PATIENT-SPECIFIC FLOWSHEETS BY ADDING/DELETING PARAMETERS

[75] Inventors: Ronald E. Norden-Paul, Peoria; Murray A. Fein, Phoenix; Sandra L. Stewart, Phoenix, all of Ariz.

[73] Assignee: Emtek Health Care Systems, Tempe, Ariz.

[21] Appl. No.: 116,611

[22] Filed: Nov. 3, 1987

[51] Int. Cl.$^4$ .............................................. G06F 15/42
[52] U.S. Cl. ................................ 364/413.01; 364/300; 364/401
[58] Field of Search ........... 364/413, 300, 401, 413.02, 364/413.01

[56] References Cited

U.S. PATENT DOCUMENTS

| | | | |
|---|---|---|---|
| 3,872,448 | 3/1975 | Mitchell, Jr. | 364/200 |
| 4,068,300 | 1/1978 | Bachman | 364/200 |
| 4,347,568 | 8/1982 | Giguere et al. | 364/300 |
| 4,570,217 | 2/1986 | Allen et al. | 364/188 |
| 4,679,137 | 7/1987 | Lane et al. | 364/188 |
| 4,791,561 | 12/1988 | Huber | 364/300 |

OTHER PUBLICATIONS

J. E. Brimm, Computers in Critical Care, Mar., 1987, pp. 53–63, Critical Care Nursing Quarterly Hewlett Packard, 78707A PDMS Clinical User's Guide, Jan. 1982, pp. i–1 thru 15–2.
Hewlett Packard, PDMS System Description, 1982, pp i–1 thru 3–6.
Health Data Sciences Corp., Ulticare TM, 1984, pp. 1–9.

Primary Examiner—Clark A. Jablon
Attorney, Agent, or Firm—Raymond J. Warren; Walter W. Nielsen

[57] ABSTRACT

A hospital information system comprises a data processing system including a plurality of terminals having display means and data entry means. Patient information is entered into the system via the terminals, is organized hierarchically in the system, and may be displayed to users having proper access to the system. Once a patient is selected from a census list, all further access to information concerning such patient is obtained in a two-level selection process by (1) selecting a descriptor corresponding to information at a first organizational level, and (2) selecting a descriptor corresponding to information at a second organization level. Various parameters can be added to or deleted from the information at the second organizational level on a patient-specific basis by an authorized system user. Certain parameters may be "pre-printed", and other parameters may represent "macro"parameters.

21 Claims, 10 Drawing Sheets

FIG. 3

METRO MEDICAL CENTER — 120

JAN 07 1000
Jackson, Donald M.  60  M  9NBURN
Attending: Charles Rice, M.D.   MR#: 87-19-46

SECTIONS: Flowsheet  Orders  NCP  Assessment  Labs  R.T.  Kardex — 152

FORMS: Meds  Vitals  I&O  Ventilator — 154

SCROLL — 155

PAGE UP — 151

| START DATE STOP DATE | MEDICATION ORDER | | 01/07 07:00 | 08:00 | 09:00 | 10:00 | 11:00 | 12:00 | 13:00 |
|---|---|---|---|---|---|---|---|---|---|
| | ROUTINE | | | | | | | | |
| 01/05/87 01/15/87 | Gentamycin IVPB  Q8H (02-10-18) | 80 mg | | | | | | | |
| 01/05/87 01/15/87 | Clindamycin IV  Q4H (00-04-08-12) | 400 mg | | 08:00 LA | | | | | |
| 01/05/87 01/15/87 | Cimetidine (Ingamet) PO  Q6H (06-10-14-18) | 200 mg (elixir) | | 08:00 LA | | | | | |
| 01/05/87 | Mylanta II PO  Q4H (06-10-14-18) | 30 cc | | | | | | | |
| | PRN | | | | | | | | |
| 01/05/87 01/08/87 | Morphine Sulfate IM  Q2H PRN Pain | 2-10 mg | 5 mg 07:00 LA site: RD | | 5 mg 09:00 LA site: LD | HELD 10:00 LA | | | |
| 01/05/87 01/08/87 | Diazepam (Valium) IV  Q4H PRN Anxiety | 2-10 mg | 2 mg 07:00 LA | 2 mg 08:00 LA | 2 mg 09:30 LA | | | | |
| 01/05/87 01/08/87 | Chlorpromazine (Thorazine) 20 mg IM  Q6H PRN Hiccups | | 20 mg 07:30 LA site: LD | | | | | | |

ADD MED — 159    PAGE DOWN — 161    D/C ALL MEDS — 153    CLOSE CHART — 163

FIG. 4

| METRO MEDICAL CENTER | | | | | | | | | | JAN 07 14:00 |
|---|---|---|---|---|---|---|---|---|---|---|
| Blood Gas Results Ready | | | | | Jackson, Donald M. 60 M | | | | | 9NBURN |
| | | | | | Attending: Charles Rice, M.D. | | | | | MR#: 87-19-46 |
| SECTIONS: | Flowsheet | Orders | NCP | Assessement | Ventilator | Labs | R. T. | Kardex | | |
| FORMS: | Meds | Vitals | I&O | Labs | | | | | | |
| | 01/07 07:00 | 08:00 | 09:00 | 10:00 | 11:00 | 12:00 | 13:00 | 14:00 | 15:00 | 16:00 |
| TEMP | 98.6 | | | | | | | | | |
| HEART RATE | 90 | 80 | 60 | 89 | 95 | 96 | 100 | 85 | | |
| BP SYSTOLIC/DIASTOLIC | 100/60 | 105/65 | 110/60 | 160/90 | 160/95 | 120/80 | 150/60 | 100/80 | | |
| (MEAN) (SOURCE) | (73) | (78) | (76) | (113) | (116) | (93) | (90) | (85) | | |
| PA SYSTOLIC/DIASTOLIC | | 30/10 | | 30/10 | | 35/15 | | 30/10 | | |
| (MEAN) | | (17) | | (17) | | (22) | | (17) | | |
| HEMO C.V.P. | | 8 | | 8 | | 10 | | 8 | | |
| C.O. | | 4.0 | | | | 5.2 | | | | |
| C.I. | | 2.18 | | | | 2.84 | | | | |
| S.V.R. | | 1180 | | | | 1080 | | | | |

PAGE UP — 151
PAGE DOWN — 153
ADD PARAMETER — 162
CLOSE CHART — 164
ADD FORM — 160
SCROLL — 155

| METRO MEDICAL CENTER | | | | | | | | | | JAN 07 14:00 |
|---|---|---|---|---|---|---|---|---|---|---|
| Blood Gas Results Ready | | | | | Jackson, Donald M. 60 M 9NBURN | | | | | |
| | | | | | Attending: Charles Rice, M.D. | | | | | MR#: 87-19-46 |
| SECTIONS: | Flowsheet | Orders | NCP | Assessement | Labs | | R. T. | Kardex | | |
| FORMS: | Meds | Vitals | I&O | Labs | Ventilator ~151 | | | | | |
| | | | | | PAGE UP | | | | | |
| | | 01/07 07:00 | 08:00 | 09:00 | 10:00 | 11:00 | 12:00 | 13:00 | 14:00 | 15:00 | 16:00 |
| TEMP ~310 | | 98.6 | | | | | | | | | |
| HEART RATE | | 90 | 80 | 60 | 89 | 95 | 96 | 100 | 85 | | |
| BP | SYSTOLIC / DIASTOLIC | 100/60 | 105/65 | 110/60 | 160/90 | 160/95 | 120/80 | 150/60 | 100/80 | | |
| | (MEAN) (SOURCE) | (73) | (78) | (76) | (113) | (116) | (93) | (90) | (85) | | |
| PA | SYSTOLIC / DIASTOLIC | | 30/10 | | 30/10 | | 35/15 | | 30/10 | | |
| | (MEAN) | | (17) | | (17) | | (22) | | (17) | | |
| HEMO | C.V.P. | | 8 | | 8 | | 10 | | 8 | | |
| | C.O. | | 4.0 | | | | 5.2 | | | | |
| | C.I. | | 2.18 | | | | 2.84 | | | | |
| | S.V.R. | | 1180 | | | | 1080 | | | | |
| | | | | PAGE DOWN ~153 | | | | | | | D/C PARAMETER ~166 |

FIG. 6

| VITAL SIGNS PARAMETERS | | | |
|---|---|---|---|
| PARAMETER NAME | [ | CO | ]—270 |
| GROUP NAME | [ | HEMO | ]—280 |
| SOURCE LIST | [ | CARDIAC OUT 1 | ]—281 |
|  | [ | CARDIAC OUT 2 | ]—282 |
|  | [ |  | ]—283 |
|  | [ |  | ]—284 |
| ASSOCIATED | [ | CI | ]—285 |
| PARAMETERS LIST | [ | SVR | ]—286 |
|  | [ |  | ]—287 |
|  | [ |  | ]—288 |
| PRE-PRINTED? | [ | NO | ]—289 |
| HOSPITAL UNIT(S) | [ | 9NBURN | ]—290 |
|  | [ |  | ]—291 |
|  | [ |  | ]—292 |
|  | [ |  | ]—293 |
| ORDER TYPE(S) | [ |  | ]—294 |
|  | [ |  | ]—295 |

┌301─┐   ┌302───┐   ┌303──┐
│ ADD │   │MODIFY│   │DELETE│
└─────┘   └──────┘   └─────┘

FIG. 8

METHOD FOR GENERATING PATIENT-SPECIFIC FLOWSHEETS BY ADDING/DELETING PARAMETERS

RELATED INVENTION

System Control Structure of a Hospital Information System and Method of Using Same, invented by John Brimm, Oscar Diaz, Ron Norden-Paul, and Michael Stern, U.S. Ser. No. 116,614, filed on even date herewith, and assigned to the assignee of the present invention.

TECHNICAL FIELD

This invention relates generally to automated hospital information systems, and, in particular, to a hospital information system in which an authorized user may add patient-specific parameters to a system form or delete such parameters.

BACKGROUND OF THE INVENTION

The present invention concerns an automated clinical records management system. Such system has utility, for example, in a hospital-based patient record-keeping system. Patient record-keeping systems are used for maintaining a wide variety of types of medical records concerning clinic or hospital patients.

Hand-written patient record-keeping systems have evolved through many years of careful refinement and enhancement into systems which maintain a detailed manual record of medical information concerning each patient. To meet the needs of different hospital entities, (such as doctors, nurses, pharmacy, accounting, laboratory, etc.) requiring access to such medical information, in a manual record-keeping system various medical information is logged into multiple types of records.

In a typical manual patient record-keeping system a patient chart, usually in the form of a notebook, is maintained at the nursing station for each patient. The notebook is divided into a plurality of individual tabbed sections, such as Physicians Orders, Kardex, Nursing Care Plan, Nursing Assessment, and Laboratory.

Each of the above sections is further subdivided into a number of forms. The forms are those which are appropriate to the individual patient and/or such patient's physician. For example, within the "Laboratory" section there may appear forms for Chemistry, Hematology, Blood Gas, and Microbiology.

In addition, a "Flowsheet" chart is usually kept at the patient's bedside. On the "Flowsheet" chart there typically appear individual areas for Medications Records, Vital Signs, Intake/Output, Laboratory Results, and other categories which are dependent upon the patient's affliction, such as Ventilator, which would be used if a patient were placed on a ventilator.

One problem with a manual patient record-keeping system is the necessity to enter the patient name and associated personal identifying information such as i.d. number, bed location, etc. separately on each patient record form associated with a given patient. This is typically done using an embossed card, similar to a credit card, containing the patient's personal information. However, this process consumes a certain amount of time, and errors may result if two patients' cards are inadvertently switched.

Another problem with manual patient record-keeping systems is that, to meet the diverse requirements of the different hospital entities for whose benefit such patient records are kept, identical information must be recorded on different forms. Again this involves additional time-consuming work and frequently causes errors to be interjected into the patient records. In addition, desired patient information may be inaccessible to a legitimate user because it is stored on a form with which such user is unfamiliar or on a form which is being accessed by another user at that time.

It has been estimated that nurses salaries account for 30%–40% of a hospital's operating budget, and that they spend 25%–40% of their time performing clerical and communications tasks. Because of changes in government regulation, insurance reimbursement policies, and competition, hospitals are increasingly under pressure to reduce their operational costs. As a result, hospital occupancy and patient length of stay have decreased, and more hospital patients are acutely ill. However, staffing levels have been reduced to cut costs. Thus, hospitals are providing care for sicker patients with fewer people, and there is a significant need for making those people more productive through hospital automation.

To maximize the productivity of hospital staff and to maximize overall patient care by making optimum use of patient data, various automated clinical record-keeping systems have been proposed and even implemented.

While automated record-keeping systems are known which organize many types of information, including information relating to customers, clients, and even medical/dental patients, no automated clinical records management system is known which provides the unmistakable benefits of an automated system and yet which very closely parallels the organization and appearance of the conventional, familiar manual hospital records charting system.

In known automated hospital record-keeping systems the user interface is typically "machine-oriented" rather than "user-friendly". The user often must proceed several layers deep through a confusing hierarchy of on-screen menus to the desired screen level. Once there, it is all too easy for the user to forget which screen level he is working in, how he got there, how to return to a more fundamental screen level, and how to move to a different screen level or to a related screen level.

Another problem with known automated patient record-keeping systems is their inflexibility regarding the user's ability to change the types and appearances of the on-screen records visually presented to the user. For example, to meet the preferences of individual hospitals, the system should be easily modified by a hospital system administrator to accommodate the particular sections and forms in use by a given hospital.

In addition, the form(s) applicable to a given patient should be capable of being amended in accordance with a change in such patient's condition. For a given physician, the relevant patient records for two different patients may vary considerably.

In known automated patient record-keeping systems the number and type of parameters displayed for a given form is predetermined and cannot be amended by the user. Typically those parameters which were displayed for any given form were those most likely to be used. However, this had the disadvantages that, for a given patient, certain parameters were unavailable, and that for many of those parameters that were available there were often large open spaces containing no values, making it difficult to read what charting information there was on the form.

It is therefore desirable that authorized users of automated patient record-keeping systems be given the ability to change the format of the on-screen forms to suit the needs of the hospital or patient care area (i.e. ward or unit), of the system user (i.e. physician or nurse), and of the patient.

In particular it is desirable to provide an authorized user with the ability to add one or more new parameters to an on-screen form to enable charting of such parameter(s) for a given patient. The type of parameters which may be added will depend upon the type of form.

Likewise, it is desirable that authorized users be given the ability to delete one or more parameters from a form if charting such parameter is not being performed or is discontinued.

In current manual patient charting systems, certain parameters tend to be added as a group. For example, if Cardiac Outputs are measured on a patient, then the clinician will also want to record Cardiac Index and Systemic Vascular Resistance. Thus it would be desirable in an automated record-keeping system to define a macro-parameter (e.g. Cardiac Outputs) whose addition will automatically add the two related parameters, Cardiac Index and Systemic Vascular Resistance, instead of requiring the user to enter each of these three parameters separately. It should be understood that the members of the macro group should still be independent for purposes of entering measurements.

Similarly, it would be desirable that if a macro-parameter, or any one of the parameters related to it, is deleted, when such parameter is no longer needed, then all of the related parameters are also deleted from the Form.

It would also be desirable to provide to the system user a form containing pre-printed parameters, thereby saving the user the effort of adding such parameters. The specific default parameters should preferably be a function of one or more of the following: the patient's admitting orders, the particular form, and the particular hospital unit.

BRIEF SUMMARY OF INVENTION

Accordingly, it is an object of the present invention to provide an improved automated clinical records management system.

It is also an object of the present invention to provide an automated clinical records management system whose format closely resembles that of a manual clinical records management system.

It is a further object of the present invention to provide an automated clinical records management system wherein the system user is given the ability to change the format of the on-screen forms to suit the needs of an individual patient by adding or deleting parameters.

It is an additional object of the present invention to provide an automated clinical records management system wherein the system user is given the ability to add one or more new parameters to an on-screen form regarding a specific patient.

It is yet another object of the present invention to provide an automated clinical records management system wherein the system user is given the ability to add automatically several new parameters to an on-screen form regarding a specific patient when such user adds a macro-parameter to such form.

It is another object of the present invention to provide an automated clinical records management system wherein the system user is given the ability to delete one or more new parameters from an on-screen form regarding a specific patient when such parameters are no longer needed on such form.

It is also an object of the present invention to provide an automated clinical records management system wherein the system user is provided with default parameters depending upon one or more of the following: the patient's admitting orders, the particular form, and the particular hospital unit.

These and other objects are achieved in accordance with a preferred embodiment of the invention by providing in a medical information system comprising a processing unit, a memory unit, and at least one terminal unit wherein the terminal unit comprises display means for displaying patient information to a terminal user and input means for the terminal user to enter patient information into the system and to provide commands to the system, a method of customizing the patient medical information regarding a patient, the method comprising (a) requiring the user to provide an indication of a patient identity using the input means; (b) providing to the terminal user via the display means patient information relating to the patient identity, including at least one patient parameter; (c) providing to the terminal user the option of performing a parameter operation, including creating a new parameter to be added to the patient information or deleting the at least one parameter; and (d) responsive to the entry of an appropriate command by the terminal user relating to the parameter operation, performing the parameter operation.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

FIG. 3 shows an information screen representing a MEDS Form in the FLOWSHEET Section.

FIG. 4 shows an information screen representing a VITALS Form in the FLOWSHEET Section and also illustrates other Sections and Forms headings.

FIG. 6 shows a DISCONTINUE PARAMETER icon on the VITALS Form in the FLOWSHEET Section.

FIG. 8 shows a configuration screen illustrating the use of the Vital Signs Parameters Table.

DETAILED DESCRIPTION OF THE INVENTION

SYSTEM HARDWARE

Figure 1:
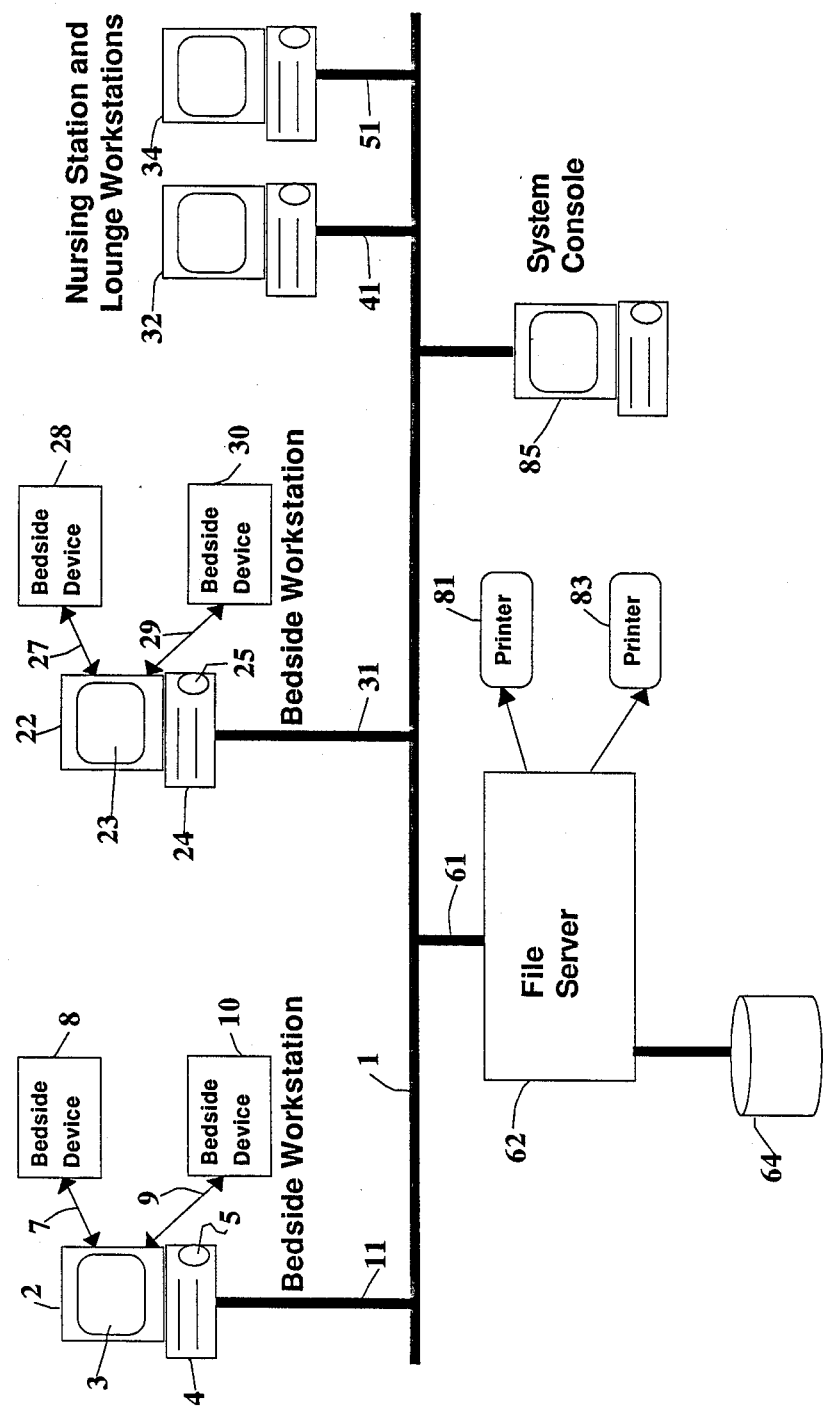
FIG. 1 shows a block diagram illustrating a preferred embodiment of a data processing system incorporating the automated clinical records system of the present invention.

Referring now to FIG. 1, a block diagram is shown of a typical hardware configuration for implementing the automated clinical records system of the present invention. FIG. 1 shows a distributed computer system comprising a plurality of workstations or terminals 2, 22, 32, 34, and 85 coupled to a local area network (LAN) 1.

The system is typically installed for use in a nursing care unit, such as an intensive care unit, in a hospital or clinic. Each of terminals 2 and 22 is located at the patient bedside. One terminal may be dedicated to the use of a single patient, or it may be used for multiple patients. Terminals 32 and 34 may be located at a nursing station or nurse/physician lounge area. Terminal 85 is the system console which is used by a system administrator to configure and maintain the system and to provide additional services, such as displaying system status and error messages, archiving, and performing diagnostics.

Each bedside workstation or terminal, such as terminal 2, includes a video display unit with a viewable screen 3 for displaying information to the viewer; a housing 4 containing computing, data storage, and communications equipment and having associated with it a keyboard and pointing device such as a mouse 5; and connections 7 and 9 to one or more bedside devices 8 and 10. Bedside devices 8 and 10 may take the form of patient monitoring equipment suitable for the patient undergoing care, such as an EKG monitor, respiratory monitor, etc. Bedside terminal 22 may be coupled to a different set of bedside devices 28 and 30 from those coupled to terminal 2.

The nursing station or lounge terminals 32 and 34, and system console 85, may be identical to those used in the patient care unit but without the bedside device connections, or they may comprise slightly different equipment (e.g. personal computers) so long as they provide similar functionality.

Also coupled to the LAN 1 is a file server 62 and associated disc storage device 64. The file server 62 provides controlled access by the workstations 2, 22, 32, 34, and 85 to write information to and read information from disc storage device 64.

Optionally coupled to LAN 1 may be interfaces (not shown) to couple various system peripheral equipment to the LAN 1. For example, remote access modems may be coupled to one of such interfaces to provide access to the system from remote terminals (not shown) located elsewhere in the hospital or located offsite, such as at a physician's residence. Remote access may also be employed to diagnose system problems from an off-site facility. A laboratory system may be connected to an interface to permit the communication of laboratory information between the laboratory system and the clinical management system. An order communication system may be coupled to an interface to permit orders to be communicated from the system to other hospital systems (e.g. pharmacy or laboratory) and vice versa. An archival storage device may be coupled to an interface to permit any information stored in the system to be safe-stored on suitable archival media, such as magnetic tapes or optical discs.

Printers 81 and 83 are coupled to file server 62 to allow patient information to be printed for the convenience of hospital personnel and to maintain a suitable legal record of all observations, orders, parameter readings, care plans, and other patient information regarding the monitored patients. Printers 81 and 83 may be any suitable printers such as, for example, laser printers or high speed dot matrix printers. A printer may optionally be coupled to the bedside terminal and/or the terminal at the nursing station or lounge, if desired.

In operation, the system user, typically a nurse or physician, conducts a dialog with the system through the use of the keyboard, mouse, or other appropriate means for entering information such as a light-pen, touch-pad, trackball, etc. "Icons", screen-sensitive areas, or the equivalent, or any combination thereof which is appropriate to the end application, may also be provided. "Icons" are symbols displayed on the screen whose functions are defined for the user by the system in view of the current screen context, and which can thus be readily changed according to the immediate requirements of the user application. In the present invention icons are selected by the system user by moving a screen cursor with the mouse and "clicking" on the icon, i.e., depressing the mouse button while the cursor overlies the icon.

The user provides information or queries to the system by means of the keyboard and/or pointing device(s), and he receives information from the system by means of information displayed on the screen and/or through audible signals which could include, in an alternative embodiment, speech synthesis.

Figure 2:
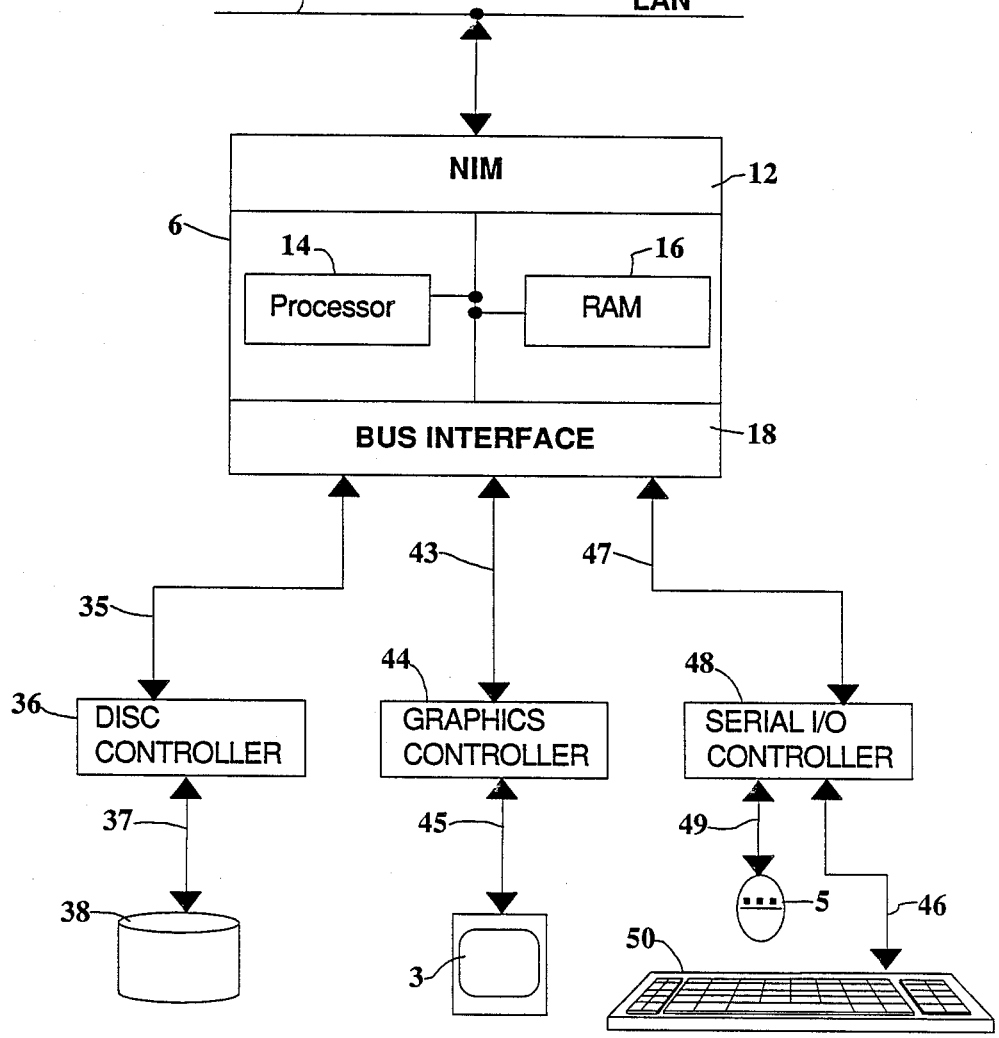
FIG. 2 shows a block diagram illustrating a processing unit associated with a workstation or terminal of the present invention.

FIG. 2 shows a block diagram illustrating a processing unit associated with a workstation or terminal of the present invention. Each terminal includes processing, storage, and communications functionality.

In FIG. 2 the Network Interface Module (NIM) 12 interfaces the terminal to the LAN 1. The terminal also comprises a processor 14, random access memory (RAM) 16, and a bus interface circuit 18. In a preferred embodiment of the invention the processor 14 is an MC68030 available from Motorola, Inc. A disc controller 36 is coupled to bus interface 18 via bus 35, and it is coupled to disc drive 38 via bus 37. A graphics controller 44 is coupled to bus interface 18 via bus 43 and to a video display unit (VDU) 3 via bus 45. A serial input-/output controller 48 is coupled to bus interface 18 via bus 47, and it is coupled to mouse 5 via bus 49 and to keyboard 50 via bus 46.

SECTIONS/FORMS HIERARCHY

As mentioned above, the automated clinical records management system of the present invention utilizes a two-level Sections and Forms organization or hierarchy, which closely resembles a manual patient charting system. This may be referred to as a "chart metaphor". Once a patient is selected from an appropriate census screen, all records pertaining to that patient are organized in a simple-to-comprehend two-level hierarchy, just as they would be if a manual record-keeping system were used.

Sections may be provided for all of the fundamental categories of patient records, such as physicians' chronological orders and active orders; organization of the orders into the Kardex and worksheet; nursing assessments; nursing care plans; documentation of therapy including fluids, medication, etc.; recording of observations including monitored variables as well as laboratory results; and organization of all patient data into flowsheets, graphs, and notes. Since the objective is to provide comprehensive computer-based bedside decision support for the clinical staff in caring for patients, the number and type of Sections and Forms will necessarily vary by hospital as well as within the hospital.

Sections and Forms will vary by hospital unit. For example, a cardiology unit will require different Sections and Forms than a pediatric unit, since they each typically have quite different patient charting requirements.

Sections and Forms will also vary according to individual physician. Thus within one hospital unit, Sections and Forms may assume one format which has been configured for nurses working within such unit. However, for a particular physician attending a patient in such unit the Sections and Forms may assume a different format.

For example, a cardiologist visiting patients in different hospital units may desire to view patient information in a particular way, concentrating on his specialty and expressed by a particular set of Sections and Forms, whereas an immunologist visiting the identical hospital units may desire to view patient information in a different way which highlights what is of special interest to him.

So Sections and Forms may be customized by hospital unit and by physician simultaneously. That is, the Sections and Forms viewed by one category of user (e.g. nurses) may differ from those viewed by a different category of user (e.g. physicians, lab technicians, etc.).

In addition to varying by system user, Sections and Forms may vary according to workstation location. For example, bedside terminals within a given ward may display a standard set of Sections and Forms for that ward (directed primarily to performing nurses' charting functions), whereas terminals in a physician's office or lounge area may display a different set of Sections and Forms (directed primarily to displaying patient information for physicians' review).

Moreover, within a particular hospital unit Sections and Forms may be modified on a patient-specific basis. For example, with a critical care unit one patient may require special dietary monitoring or social service monitoring, or another may require a respirator. So Sections and Forms may be customized by the system user to fulfill the charting requirements of individual patients.

Reference may be had to the above-identified Related Invention regarding the ability to add or delete Sections and Forms, both by the system configurer as well as by an authorized user of the system.

FIG. 3 illustrates an example of the two-level Sections/Forms organization. FIG. 3 shows an information screen representing a MEDS Form in the FLOWSHEET Section. FIG. 3 also illustrates other Sections and Forms options.

In FIG. 3, a plurality of different Sections options are displayed in area 152. The Sections displayed are Flowsheet, Orders, Nursing Care Plan (NCP), Assessment, Laboratory Results (Labs), Respiratory Therapy (R.T.), and Kardex.

Each section comprises one or more Forms which can be selected for viewing by the user. For example, in FIG. 3 the Forms corresponding to the Flowsheet Section are shown to be the Medications (Meds), Vital Signs (Vitals), Intake & Output (I&O), Laboratory Results (Labs), and Ventilator Forms. Upon first selecting a given patient the first Section (i.e. Flowsheet) and first Form (i.e. Meds) in the lists are displayed by default.

As mentioned previously, the principal method of user interaction with the system is by means of a pointing device, such as a mouse. The user is presented with the two-level organization comprising Sections and Forms, and his options at either level are clearly presented to him on the screen.

To move between the various Sections of the system the user simply points with the mouse to the appropriate Section on the Form. For example, with reference to FIG. 3, the user can move the screen cursor by means of the mouse to overlie one of the alternative Sections in area 152, such as the "ORDERS" or "NCP" Sections. When the user "clicks" on the desired Section, the system acknowledges the selection by highlighting the Section by reverse-video or other appropriate manner. At the same time, the system presents in area 154 the various Forms options corresponding to the selected Section.

If the user wishes to view a desired Form in the selected Section, the user moves the cursor to point to the desired Form option and "clicks" on it. The system responds by displaying the selected Form.

Still with reference to FIG. 3, certain features which are generic to other Forms screens are shown. For example, in the upper right-hand corner is an area 120 reserved for patient demographics, giving the patient's name, I.D. number, room number, and any other pertinent information. It is meant to resemble the "addressograph" of a manual patient record-keeping system, although additional information may be displayed as well.

In the upper left-hand corner is an area 150 reserved for messages. Such messages alert the user to new and relevant information pertaining to this patient. Such information may originate from other parts of the system. For example, referring momentarily to area 150 of FIG. 5, updated laboratory information (e.g. a blood gas result) may be supplied from the laboratory. Many other possible messages can be provided, such as updated vital signs information (e.g. a change in respiratory rate).

An important advantage of the present invention is that all portions of the system are linked so that information can be shared among Sections and Forms with a single data entry. For example, once the patient demographics have been entered for a given patient, they appear identically on every Form for that patient. Any amendment of the demographics for a given patient need be made only once, and it is automatically applied to every other Form for that patient.

With reference now to the specific content of FIG. 3, the Medications Form is used by the nurse to record medications given to the patient, as ordered by the physician. Medications may be added to or deleted from this Form as the result of physician's orders. If a medication is not administered as ordered, the nurse may indicate this, along with the reason.

In the left-hand column of area 157 of FIG. 3 appear the start and stop dates for the corresponding medication orders. The medication orders themselves are divided into Routine medication orders and PRN (i.e. as required) medication orders. All pertinent medication order information is provided including the medication name (and generic name, if available), dose, route/site, frequency, and schedule. Following the medication orders area are time columns, and at the intersection of each medication order and the appropriate time column the nurse may log information concerning the administration of the medication to the patient.

To enter an item of information into the Form, the nurse first points with the mouse to the space on the Form appropriate to the desired entry and clicks. If entry cannot be made directly onto the Form, a pop-up window appears. The nurse may then either select an item from a list of possible entries displayed in the window by moving the cursor over it and clicking with the mouse, or else, in the event that user entries cannot be anticipated, the nurse directly types information into the pop-up window. The system then responds with a view of the Form with the selected item appearing as an entry in the appropriate space of the Form. The nurse confirms the correctness of the entered data by pointing and clicking at an electronic signature area.

In order to view information which is part of the selected Form but "off-screen", the user may scroll either horizontally or vertically by clicking on the appropriate scrolling icon. For example, the user may scroll down a page in FIG. 3 by clicking on the "Page Down" icon 153 or horizontally to the right by selecting the "Scroll Right" icon 155.

FIG. 4 shows an information screen representing a VITALS Form in the FLOWSHEET Section. This Form was reached by the user from the screen shown in FIG. 3 merely by clicking on the Vitals Form. In area 150 of this screen, a message is displayed to the user concerning this patient to alert the user to new information.

In FIG. 4 a number of Vital Signs parameters relating to the selected patient are given along the left-hand side of area 156. In the illustration these parameters comprise Temperature, Heart Rate, Blood Pressure, Pulmonary Arterial Pressure, and Hemodynamics. To the right of the list of Vital Signs are time columns. Charting of Vital Signs may be done hourly, at any other selected interval, or at any selected time. At the intersection of each Vital Sign and the appropriate time column the nurse may log information concerning the patient's Vital Signs. Additionally, certain of the Vital Signs may be logged automatically at predetermined time intervals from bedside patient- monitoring equipment.

OTHER SECTIONS/FORMS OPTIONS

With reference to the information screens shown in FIGS. 3 and 4, had the user selected the ORDERS Section, typical Forms would be the ORDER SHEET and ORDER HISTORY. Under the NCP Section heading might appear the CURRENT NCP Form, and under the ASSESSMENT Section might appear the SHIFT ASSESSMENT Form.

Regarding the LABS Section, typical Forms might be CHEMISTRY, HEMATOLOGY, and MICROBIOLOGY. Another typical Section might be Respiratory Therapy, and it would typically comprise the VENTILATOR and RESPIRATORY THERAPY NOTES Forms. The Kardex Section might include Forms for a TASK LIST, DIAGNOSTIC STUDIES, MEDICATIONS, and GENERAL CARE.

It will be understood that many other possible Sections and Forms may be used, and that the foregoing are for illustrative purposes only.

"PRE-PRINTED" PARAMETERS

When the system user selects a given Form for display on the screen, a number of parameters are displayed by default. These are known as "pre-printed parameters", and they resemble the pre-printed parameters on a manual chart.

For example, with reference to FIG. 4, which shows the Vitals Form of the Flowsheet Section, the "pre-printed parameters" could be the Temperature, Heart Rate, and Blood Pressure parameters. From the first time this Form is displayed these parameters will appear on the Form without requiring the system user to add them to the Form.

The choice of the specific parameters which are "pre-printed parameters" for a given Form is determined by the system administrator and system configurer, as described below regarding FIG. 8.

The determination of which parameters are "pre-printed parameters" is a function of one or more of the following: the patient's admitting orders, the particular Form, and the particular hospital unit.

For example, when a patient is admitted to the hospital, admitting orders are customarily written for the patient by the patient's physician. Based upon predetermined types of admitting orders, certain parameters may be automatically "pre-printed" on the patient's Forms.

Also Forms may be designed such that any given Form automatically contains certain predetermined "pre-printed parameters", as shown and described above regarding FIG. 4.

In addition, a particular Form as used in one hospital unit may contain different "pre-printed parameters" from the corresponding Form as used in a different unit in the same hospital, owing to the different charting requirements of the units.

The customizing of "pre-printed parameters " is done by the system configurer, as described below regarding FIG. 8.

REAL TIME FORM MODIFICATION—ADDING/DELETING PARAMETERS

To customize the patient charts to the individual patient, the system enables the user to add and delete parameters to certain of the displayed Forms. For example, with reference to FIG. 4, the nurse may desire to begin charting a new parameter which was not "pre-printed" on the Form or to discontinue charting a previously charted parameter (whether "pre-printed" or otherwise).

In area 158 of the screen shown in FIG. 4 are displayed various icon options including the ADD PARAMETER and CLOSE CHART icons associated with window areas 162 and 164, respectively. The window displayed by the system in response to selection of the ADD PARAMETER icon 162 is illustrated by FIG. 4 which will now be discussed.

Figure 5:
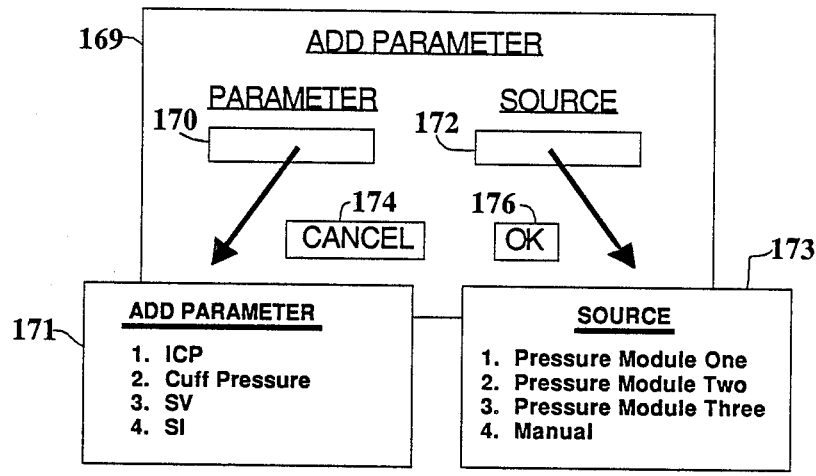
FIG. 5 shows an ADD PARAMETER information window on the VITALS Form in the FLOWSHEET Section.

FIG. 5 shows an ADD PARAMETER information window 169 on the VITALS Form in the FLOWSHEET Section. Once in the ADD PARAMETER pop-up window, the user may point and click on either the PARAMETER function 170 or the SOURCE function 172. Selection of the PARAMETER function 170 displays a further ADD PARAMETER pop-up window 171, with a list of four possible additional parameters. The user may select on any of these four and then sign-off using OK icon 176 or cancel using CANCEL icon 174 in the ADD PARAMETER information window 169.

It should be noted that the list of optional parameters to be added to a Form excludes any parameters which are already displayed on the Form.

If the user selects SOURCE icon 172, pop-up window 173 is displayed, and the user may select on any of four possible sources for the newly selected parameter and then sign-off using OK icon 176 or cancel using CANCEL icon 174.

The additional parameters and the sources listed in pop-up windows 171 and 173, respectively, are not limited in number or type, but they may be expanded, modified, or deleted at the option of the system administrator.

As shown in FIG. 6, an authorized system user may discontinue any parameter by positioning the cursor in the screen cell containing the parameter to be deleted and clicking the pointing device. In FIG. 6 the HEART RATE parameter has been selected for deletion by clicking the pointing device on area 310. This displays the parameter in inverse video. Simultaneously a D/C PARAMETER icon 166 appears in the lower part of the screen. The system user may then click on the D/C PARAMETER icon 166. This operation marks the selected parameter as discontinued and prohibits further measurement on it. If the parameter happens to be a macro-parameter, then all of its associated parameters are also automatically discontinued.

After a site-specifiable time delay, the parameter will no longer be displayed on the form, although its values may still be reviewed by scrolling the form back in time to a point before it was discontinued. The list of parameters is only adjusted once per day, at a site-specified time. This prevents excessive movement of parameter locations up and down on the form as the user scrolls time-wise through the form. This is analogous to a manual system wherein when a parameter is discontinued on a twenty-four hour flowsheet, it remains on the form until the next day's flowsheet is created, at which point the discontinued parameters are not copied forward.

SYSTEM CONFIGURATION—ADDING/DELETING PARAMETERS

Figure 7:
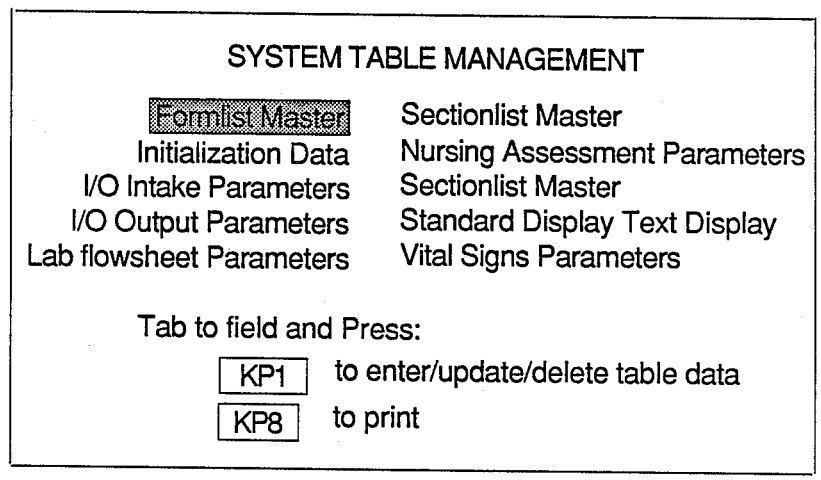
FIG. 7 shows a main configuration menu on a system configuration screen.

FIG. 7 shows a screen illustrating the system's table configuration menu labeled "System Table Management". As stated above, the clinical information system of the present invention can be configured to meet the unique requirements of an individual hospital, hospital unit, and/or individual.

Typically, a hospital system administrator and an installation specialist from the manufacturer of the present system first determine the requirements of the hospital and/or of individual hospital units regarding the parameters which should be provided as default parameters for specific Forms. They also determine which parameters will be considered optional parameters which are not default parameters but which may be added at the option of an authorized system user. In addition, they determine which parameters are macro-parameters, and they identify those parameters which are associated with each macro-parameter.

Next the hospital system administrator and installation specialist use a Form Editor to create all the Forms to be used in the system. Each Form requires a definition that specifies the data content of the Form, along with the visual appearance of that data. Each Form is assigned a Form ID which is used to identify the Form in the Formlist Master, described below.

Next the hospital system administrator and installation specialist generate the parameter lists for each Form. These parameter lists define the candidate parameters and macro-parameters for each Form, as well as the candidate sources for each parameters (as in the case of candidates sources 281–284 described below with reference to FIG. 8).

Next the hospital system administrator and installation specialist generate the Sectionlist Master and Formlist Master tables. The Sectionlist Master table is a Section configuration table, each record of which represents a different Section which could reasonably be utilized in the system as customized for this particular hospital. Likewise, the Formlist Master table is a configuration table, in which each record represents a different Form which could feasibly be utilized in the system.

By using the system's table configuration menu, the hospital system administrator can thus at any time modify the system for the hospital as an entity or for individual hospital units. Thus, if after a period of use of the system, the hospital system administrator determines that the system, as used by the hospital as a whole or by an individual unit, should contain additional default parameters or additional macro-parameters for a particular Form, the system administrator may utilize the appropriate table of the table configuration menu (FIG. 7) to make such change. Likewise, the hospital system administrator may delete parameters with regard to any Form, either on a hospital-wide basis or for an individual hospital unit.

The system configuration information is contained within a software database. The database used to implement a preferred embodiment of the invention is known as the Empress database, commercially available from Rhodnius, Inc., Toronto, Canada. However, the invention is not limited to the use of any one database.

As shown in FIG. 7 the system's table configuration menu comprises the following configuration table options which are relevant to this invention: an I/O Intake Parameters tble, an I/O Output Parameters table, a Lab Flowsheet Parameters table, a Nursing Assessment Parameters table, and a Vital Signs Parameters table.

The I/O Intake Parameters table specifies a list of I/O Intake Parameters which can be added to or deleted from the Input & Output Form of the Flowsheet Section of the system.

The I/O Output Parameters table specifies a list of I/O Output Parameters which can be added to or deleted from the Input & Output Form of the Flowsheet Section of the system.

The Lab Flowsheet Parameters table specifies a list of Lab Flowsheet Parameters which can be added to or deleted from the Labs Form of the Flowsheet Section of the system.

The Nursing Assessment Parameters specifies a list of Nursing Assessment Parameters which can be added to or deleted from the Assessment Form of the Flowsheet Section of the system.

The Vital Signs Parameters specifies a list of Vital Signs Parameters which can be added to or deleted from the Vitals Form of the Flowsheet Section of the system.

FIG. 8 shows a configuration screen illustrating the use of the Vital Signs Parameter Table, which is used to specify both the default (i.e. pre-printed) and optional Vital Signs Parameters regarding the Vital Signs Form of the Flowsheet Section. The Vital Signs Parameters Table is called up from the main table configuration menu shown in FIG. 7 by appropriately selecting it, either by using the tab key to move through the list of table options or by typing in the name of the desired table.

Basically, the configuration file for the Vital Signs Parameters Table comprises a plurality of database "records" each corresponding to a different Vital Signs parameter. Each record comprises a plurality of "data fields" which contain information about the content and layout of the selected parameter.

The screen shown in FIG. 8 contains three icons 301, 302, and 303 along the bottom, representing the ADD PARAMETER, MODIFY PARAMETER, and DELETE PARAMETER icons, respectively. Selecting any one of these icons results in the corresponding command being executed, thereby enabling a system configurer to add a new parameter, modify an existing parameter, or delete an existing parameter.

The addition of a new parameter by the system configurer is accomplished by selecting the ADD PARAMETER icon 301 and then filling in the fields on the screen describing the new parameter. The system configurer may move from one data field 270–289 in the table to another data field by tabbing or other appropriate means.

The first field 270 in the table is for the name of the parameter to be added, which in the example shown is Cardiac Output (CO).

The group name field 271 allows this parameter to be placed on the patient form under a group label heading with other parameters having the same group label. In the example shown in FIG. 8 the group name is Hemodynamics (HEMO). Referring momentarily to information area 156 of FIG. 4, it will be seen that the "HEMO" group namme is given to the group of related parameters identified as "C.V.P.", "C.O.", "C.L.", and "C.V.R.". The group name is merely a designator which appears on the screen with reference to a group of related parameters. It should not be confused with a macro-parameter.

The source list fields 281–284 are used to provide a set of names of patient device data channels which can be used to default the value of the parameter when the user is charting it. The source list is used to generate the candidate list of sources 173 (FIG. 5) presented to the system user when the system user is adding a parameter.

The associated parameters list fields 285–288 are used to establish a macro-parameter and its related parameters. Any parameters entered into fields 285–288 will automatically be added to the Form whenever the primary parameter (i.e. the one appearing in field 270) is added to the Form by the system user. Likewise, such parameters will automatically be deleted whenever the primary parameter is deleted from the Form by the system user.

The pre-printed field 289 is used to indicate whether the parameter is to be pre-printed (i.e. defaulted) on the Form when the patient is first admitted to the system. In the example shown, the indication is "No". If the indication had been "Yes", the system configurer could have further indicated, by appropriate entry into fields 290–293, the names of which hospital unit(s) the parameter should be automatically pre-printed on the Form upon admission of a patient into one of such designated hospital units. For example, if the indication in field 289 had been "Yes" and the "CARDIAC UNIT" had been indicated in field 290, then the "CO" parameter would automatically appear in every Vital Signs Form for each patient admitted to the Cardiac Unit.

The system configurer could also indicate by entry of appropriate information into fields 294 and 295 the patient order type(s) for which the parameter should be automatically pre-printed.

The system configurer may modify existing parameter entries in the Vital Signs Parameter Table by entering an existing parameter name in the parameter name field 270 and selecting the MODIFY icon 302. The existing data fields for that parameter are then displayed, and the system configurer may modify them, in a similar manner to the way in which the information was originally entered into such data fields. The selection of another command icon 301–303 or exiting the screen automatically saves the modified values.

The system configurer may delete an existing parameter by entering an existing parameter in the parameter name field 270 and selecting the DELETE icon 303.

SYSTEM SECURITY

The system security aspects will now be discussed. In general, users must present not only a user log-on identification number but also a personal password. Both the user I.D. number and personal password must be entered through the keyboard; the password is ordinarily not echoed to the screen.

Access privileges may be defined for specific groups of users, such as nurses, physicians, therapists, and lab technicians. Privileges may also vary according to the particular Section or Form, the particular patient, the particular user, and the particular terminal location. Privileges may also vary within a given Form, regarding whether access is read-only or read-write. Certain Forms can be read without logging on, just as certain handwritten Forms can presently be read without requiring a signature.

However, all additions or deletions of parameters to or from Forms require the identification of a responsible user, and thus the system requires logging on in order to make such a change to a Form.

To implement the security features of the system, the system administrator and manufacturer's installation specialist use a security editor to define the conditions for accessing and/or modifying the various Sections and Forms of the system. This generates the proper access entitlements discussed above.

Figure 9A:
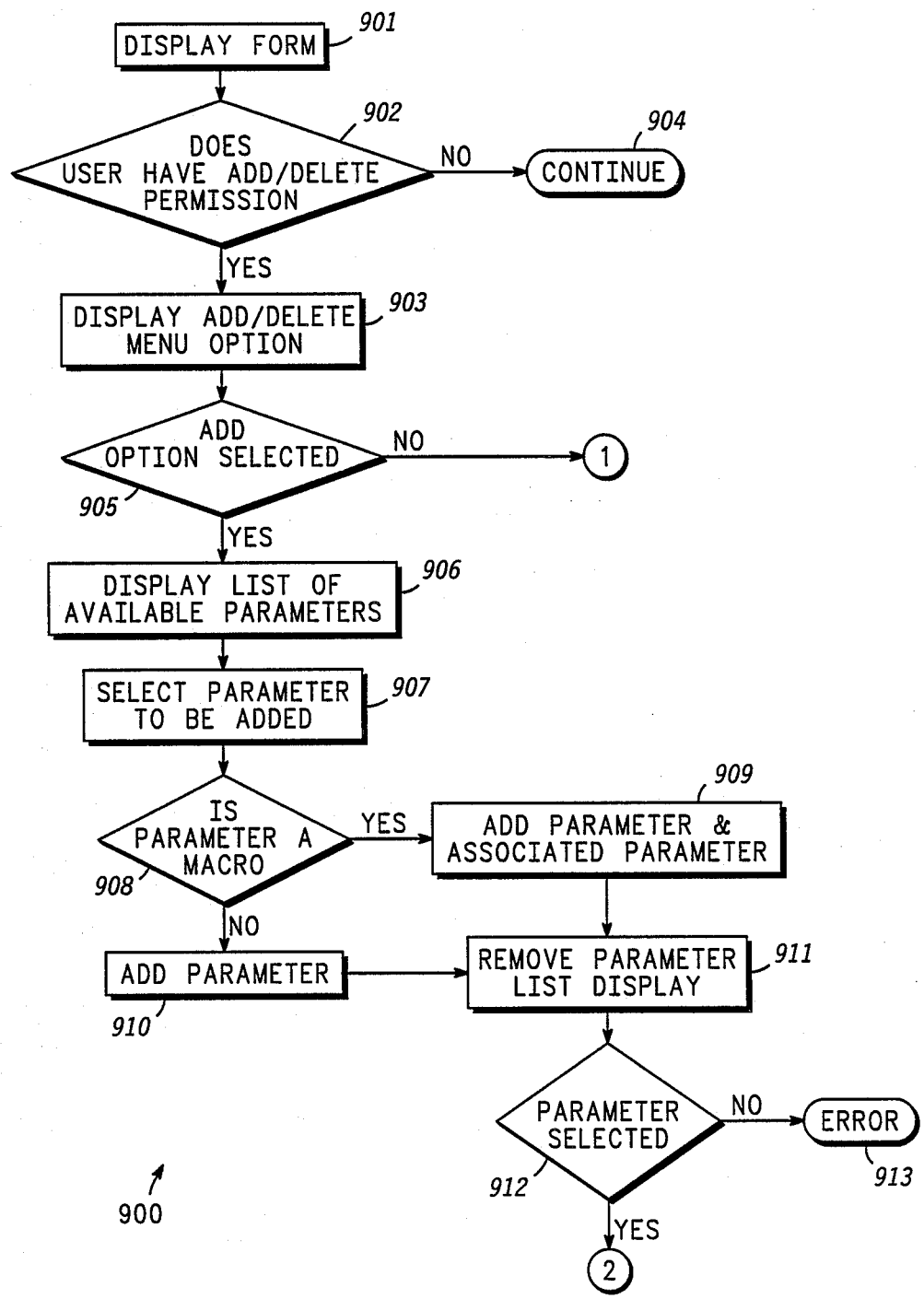
FIGS. 9A–9C show a flow chart embodying the present invention.
Figure 9B:
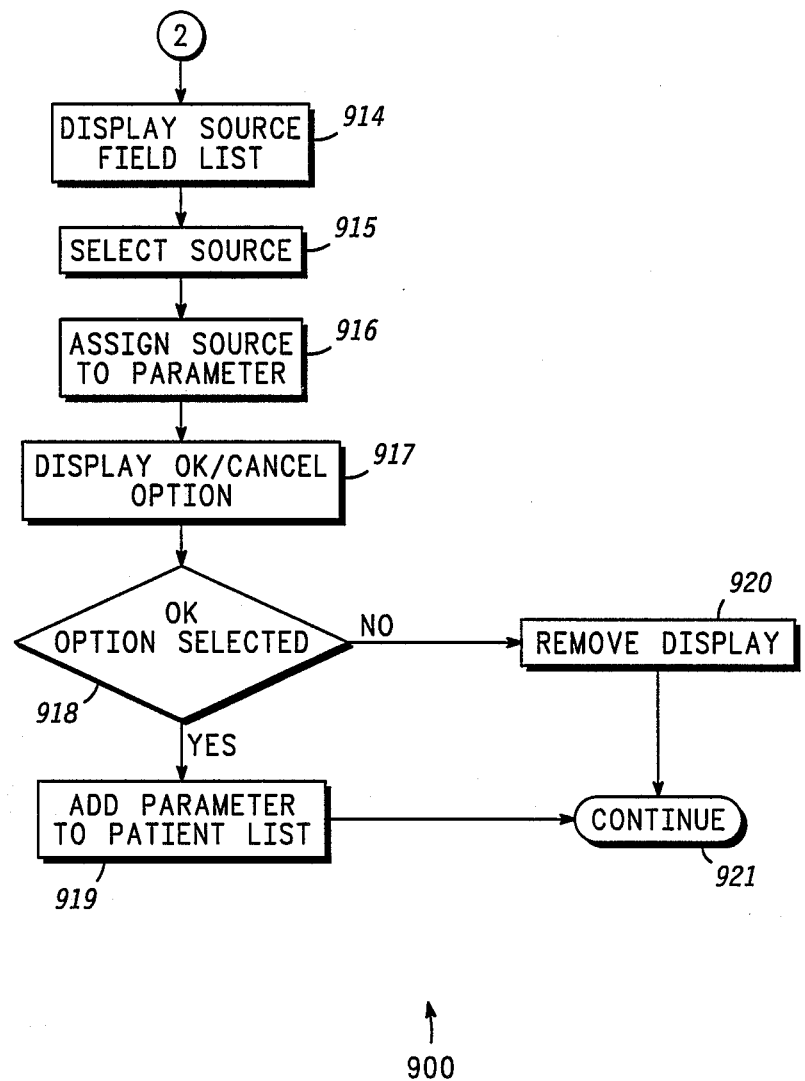
Figure 9C:
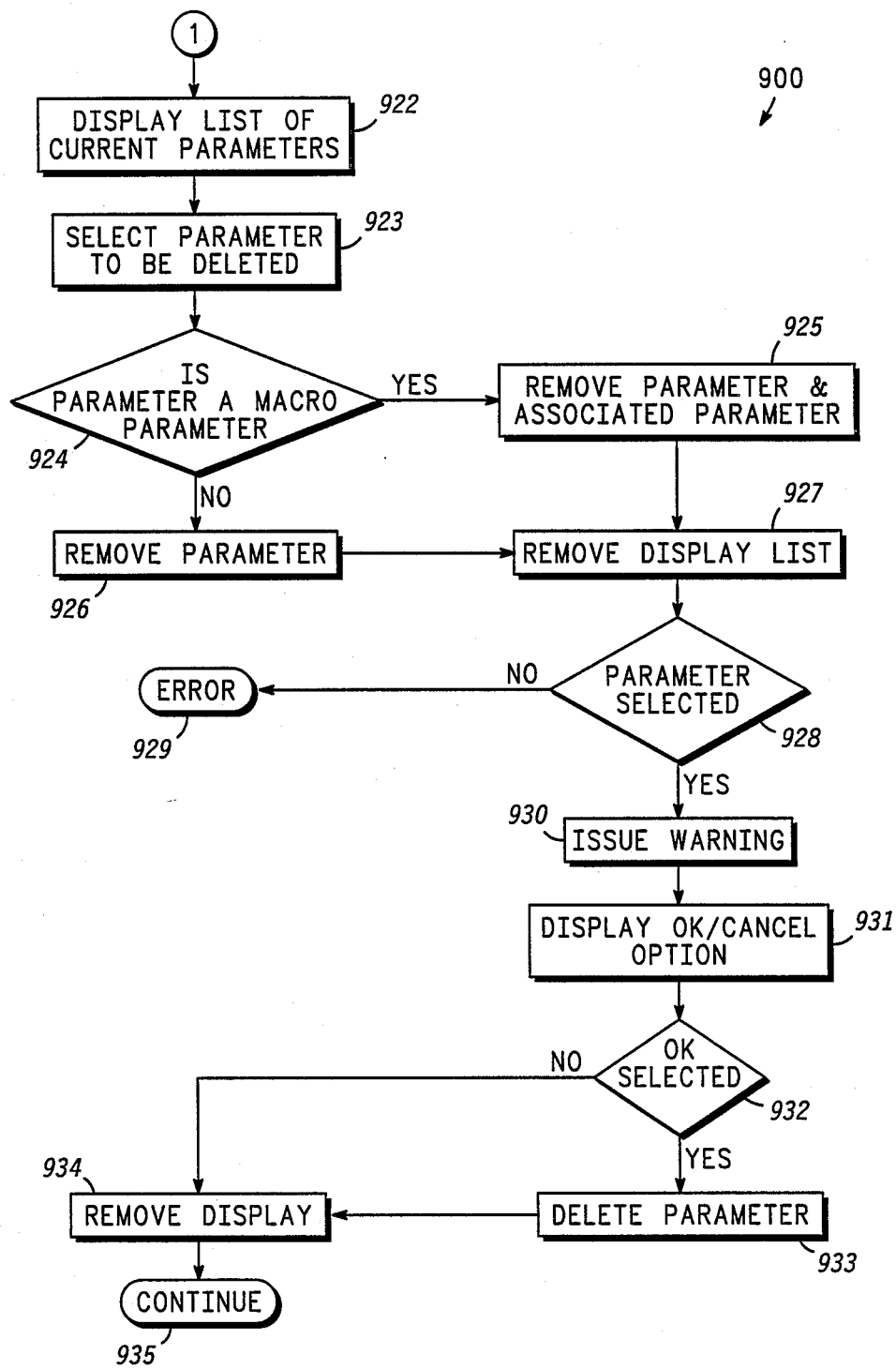

Referring now to FIGS. 9A–9C, a flow chart, generally designated 900, embodying the present invention is illustrated. The process commences with a form being displayed (step 901) such as the VITALS form of FIG. 4. When the user selects a form, the system will determine if the user has permission to add/delete parameters (step 902).

If the user has add/delete permission, the add option, block 164 of FIG. 4, and/or the delete option, block 166 of FIG. 5, will be displayed (step 903). If the user does not have permission, these menu options are not displayed and the process continues (step 904).

If the add option is selected (step 905) a list of available parameters will be displayed (step 906) such as shown in FIG. 5. The parameter to be added is then selected (step 907).

Upon selecting a parameter, the process determines if the selected parameter is a macro parameter (step 908). If the parameter selected is a macro parameter, the parameter and its associated parameters are identified for addition (step 909). Otherwise, only the selected parameter is identified for addition (step 910).

After the parameters have been identified for addition, the list of displayed parameters is removed (step 911). If a parameter was not selected (step 912) an error will result (step 913). If a parameter was selected, a source field list will be displayed (step 914) such as list 173 of FIG. 5. A source is then selected (step 915) and assigned to the parameter (step 916).

Following the source selection, the OK and CANCEL options (items 176 and 174, respectively, of FIG. 5) are displayed (step 917). If the OK option is selected (step 918), the parameter is added to the patient list (step 919). If the OK option is not selected, the display is removed (step 920). From this point, the process continues (step 921).

If the add option is not selected from the add/delete menu (step 905), the system will display a list of current parameters (step 922) from which a parameter to be deleted may be selected (step 923).

The process then determines if the parameter is a macro parameter (step 924). If the parameter is a macro parameter, the macro parameter and its associated parameters are selected for removal (step 925). If the parameter is not a macro parameter, the parameter is selected for removal (step 926). The display list is then removed (step 927). If no parameters were selected (step 928), an error will result (step 929). If a parameter was selected, a warning is issued (step 930) and an OK/CANCEL option is provided (step 913).

If the OK option is selected (step 932), the parameter is deleted (step 933). Following the deletion, or if the OK option is not selected, the display is removed (step 934) and the process continues (step 935).

DISCUSSION OF APPENDIX

The APPENDIX provides a pseudo-code listing of the software for adding and/or deleting a parameter and a macro-parameter.

It will be apparent to those skilled in the art that the disclosed invention may be modified in numerous ways and may assume many embodiments other than the preferred form specifically set out and described above.

For example, the selection and number of parameters which may be utilized on a Form may be determined to meet the particular requirements of the system users and the patients.

Accordingly, it is intended by the appended claims to cover all modifications of the invention which fall within the true spirit and scope of the invention.

APPENDIX

PSEUDO-CODE FOR ADDING/DELETING
A PARAMETER OR MACRO-PARAMETER.

```
Display Add_Parameter pop-up form
Case  (parameter field selected):
      Generate list of candidate parameters as logical Exclusive
      OR of (all possible parameters for Vital Signs Form) and
      (parameters assigned to currently selected patient)
      Display list to screen
      EndCase
Case  (choice from parameter list selected):
      If (parameter is a macro-parameter)
         add chosen parameter and all associated parameters to
         the list of parameters for the patient
      Else
         add chosen parameter to list of parameters for the
         patient
      Remove parameter list from screen
      Move cursor to source field
      EndCase
```

APPENDIX-continued

PSEUDO-CODE FOR ADDING/DELETING
A PARAMETER OR MACRO-PARAMETER.

```
Case  (Source field selected):
      If (value has been entered into parameter field)
         Generate list of candidate sources assigned to
         parameter entered in parameter field
         Display list to screen
      EndIf
      Else
         Display error message to user
      EndCase
Case  (choice from source list selected)
      Assign selected source to currently entered parameter
      Move cursor to parameter field
      EndCase
Case  (OK icon selected)
      Commit new parameter(s) to parameter list for current
      patient
      Remove pop-up form from screen
      EndCase
Case  (CANCEL icon selected)
      Remove pop-up form from screen
      EndCase
```

What is claimed is:

1. In a medical information system comprising a processing unit, a memory unit, and a terminal unit wherein said terminal unit comprises display means for displaying a patient medical information form to a terminal user and input means for said terminal user to enter patient information into said system and to provide commands to said system, a method of customizing said patient medical information form comprising:
   (a) providing to said system an indication of a patient identity using said input means;
   (b) providing to said terminal user, via said display means, said patient medical information form relating to said patient identity;
   (c) selecting a parameter operation, said parameter operation including adding a new parameter to said patient medical information form or deleting a selected parameter from said patient medical information form;
   (d) performing said parameter operation by deleting said selected parameter if said deleting parameter operation was selected in step (c); and
   (e) performing said parameter operation by adding said new parameter if said adding parameter operation was selected in step (c).

2. The method as recited in claim 1, wherein the option provided in step (c) is in response to the entry of an appropriate command by said terminal user.

3. The method as recited in claim 1, wherein in step (c) said parameter is a macro parameter, and wherein in steps (d) or (e) the performance of said parameter operation causes an associated parameter to be added or deleted automatically with said macro parameter.

4. In a medical information system comprising a processing unit, a memory unit, and a terminal unit wherein said terminal unit comprises display means for displaying a patient medical information form to a terminal user and input means for said terminal user to enter patient information into said system and to provide commands to said system, a method of customizing said patient medical information form comprising:
   (a) providing an indication of a patient identity using said input means;
   (b) providing to said terminal user, via said display means, patient information relating to said patient identity, including a plurality of form options each containing patient information;
(c) selecting one of said form options;
(d) displaying a selected form;
(e) selecting a parameter operation, said parameter operations including adding a new parameter to said selected form or deleting a selected parameter from said selected form;
(f) performing said parameter operation by deleting said selected parameter if said deleting parameter operation was selected in step (e); and
(g) performing said parameter operation by adding said new parameter if said adding parameter operation was selected in step (e).

5. The new method as recited in claim 4, wherein in step (e) the choice of said new parameter is dependent upon the selected form.

6. The method as recited in claim 4 wherein said selected form includes at least one parameter.

7. The method as recited in claim 6, wherein said new parameter is different from said at least one parameter.

8. The method as recited in claim 6, wherein said at least one parameter is dependent upon the selected form.

9. The method as recited in claim 8, wherein said at least one parameter is dependent upon an admitting order of said patient.

10. The method as recited in claim 8, wherein said at least one parameter is dependent upon a hospital unit in which said patient is located.

11. In a medical information system comprising a processing unit, a memory unit, and a terminal unit wherein said terminal unit comprises display means for displaying a patient medical information form to a terminal user and input means for said terminal user to enter patient information into said system and to provide commands to said system, a method of selectively granting access to said terminal user to customize said patient medical information form, said method comprising:
(a) providing an indication of said user's identity using said input means;
(b) providing an indication of a patient identity using said input means;
(c) providing to said terminal user, via said display means, said patient medical information form;
(d) providing to said terminal user the option of performing a parameter opertion, including adding a new parameter to said patient medical information form or deleting a selected parameter from said patient medical information form;
(e) selecting said parameter operation;
(f) utilizing said terminal user's identity to determine whether said terminal user has permission to perform said selected parameter operation; and
(g) performing said parameter operation if said terminal user has permission, otherwise denying said terminal user the right to perform said selected parameter operation.

12. The method as recited in claim 11, wherein the option provided in step (d) is in response to the entry of an appropriate command by said terminal user.

13. The method as recited in claim 11, wherein in step (d) a selected one of said new parameter or said selected parameter is a macro parameter, and wherein in step (g) the performance of said parameter operation causes an associated parameter to be added or deleted with said macro parameter.

14. In a medical information system comprising a processing unit, a memory unit, and a terminal unit wherein said terminal unit comprises display means for displaying a patient medical information form to a terminal user and input means for said terminal user to enter patient information into said system and to provide commands to said system, a method of customizing said patient medical information form comprising:
(a) providing an indication of said terminal user's identity using said input means;
(b) providing an indication of a patient identity using said input means;
(c) providing to said terminal user, via said display means, said patient information form, including a plurality of form options;
(d) selecting one of said form options;
(e) displaying a selected form;
(f) selecting a parameter operation, said parameter operation including adding a new parameter to said selected form or deleting a selected parameter from said selected form;
(g) utilizing said terminal user's identity to determine whether said terminal user has permission to perform said selected parameter operation; and
(h) performing said parameter operation is said user has permission, otherwise denying said terminal user the right to perform said selected parameter operation.

15. The method as recited in claim 14, wherein in step (f) the choice of said new parameter is dependent upon the selected form.

16. The method as recited in claim 1, wherein said new parameter is different from said at least one parameter.

17. The method as recited in claim 1, wherein said at least one parameter is dependent upon the selected form.

18. The method as recited in claim 17, wherein said at least one parameter is dependent upon an admitting order of said patient.

19. The method as recited in claim 17, wherein said at least one parameter is dependent upon a hospital unit in which said patient is located.

20. The method as recited in claim 14 wherein said selected form includes at least one parameter.

21. In a medical information system comprising a processing unit, a memory unit, a terminal unit wherein said terminal unit comprises display means for displaying a patient medical information form to a terminal user and input means for said terminal user to enter patient information into said system and to provide commands to said system, and a parameter set including a macro parameter and an associated parameter, a method of customizing said patient medical information form comprising:
(a) providing to said system an indication of a patient identity using said input means;
(b) providing to said terminal user, via said display means, said patient medical information form relating to said patient identity;
(c) selecting a parameter operation, said parameter operation including adding a new parameter to said patient medical information form or deleting a selected parameter from said patient medical information form;
(d) performing said parameter operation by deleting said selected parameter if said deleting parameter operation was selected in step (c);

(e) deleting said associated parameter if said selected parameter in step (d) is said macro parameter;

(f) performing said parameter operation by adding said new parameter if said adding parameter operation was selected in step (c); and (g) adding said associated parameter if said new parameter in step (f) is said macro parameter.

* * * * *